(12) United States Patent
Takahashi et al.

(10) Patent No.: US 7,857,897 B2
(45) Date of Patent: Dec. 28, 2010

(54) AIR FILTERING APPARATUS

(75) Inventors: Kazuo Takahashi, Gunma (JP); Yoichi Uchida, Tochigi (JP); Hiroaki Usui, Gunma (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 413 days.

(21) Appl. No.: 11/837,838

(22) Filed: Aug. 13, 2007

(65) Prior Publication Data

US 2008/0041230 A1 Feb. 21, 2008

(30) Foreign Application Priority Data

Aug. 21, 2006 (JP) .............................. 2006-223986

(51) Int. Cl.
*B01D 47/02* (2006.01)
(52) U.S. Cl. .............................. 96/236; 96/296; 96/297
(58) Field of Classification Search .................. 96/243, 96/236, 234, 296, 297
See application file for complete search history.

(56) References Cited

U.S. PATENT DOCUMENTS

2004/0013563 A1* 1/2004 Romer et al. .................. 422/28

FOREIGN PATENT DOCUMENTS

| JP | 62069033 A | 3/1987 |
|---|---|---|
| JP | 2000-257914 A | 9/2000 |
| JP | 2000-334240 A | 12/2000 |
| JP | 2002-181358 A | 6/2002 |
| JP | 2003-172531 A | 6/2003 |
| WO | WO-01/90001 A | 11/2001 |

OTHER PUBLICATIONS

Office Action mailed on Aug. 4, 2009 in corresponding Canadian Patent Application No. 2,595,662.

* cited by examiner

*Primary Examiner*—Duane Smith
*Assistant Examiner*—Tiffany N Palmer
(74) *Attorney, Agent, or Firm*—Westerman, Hattori, Daniels & Adrian, LLP

(57) ABSTRACT

An air filtering apparatus including a housing having an air suction port through which air is sucked and an air blow-out port through which air is blown out, an air blower for forming in the housing an air flowing passage through which the air sucked from the air suction port flows to the air blow-out port, an air filtering unit that is disposed on the air flowing passage and brings the air supplied along the air flowing passage into contact with electrolytic water containing active oxygen species to filter the air, an electrolytic water supply unit for electrolyzing prescribed water to generate the electrolytic water and supplying the electrolytic water to the air filtering unit, and a water supply unit having a water stock unit for stocking the prescribed water supplied through a water distributing pipe from an external water supply source, the water stocked in the water stock unit being supplied to the electrolytic water supply unit, wherein the air filtered by the air filtering unit is blown out from the air blow-out port to a room.

10 Claims, 6 Drawing Sheets

AIR FILTERING APPARATUS

INCORPORATION BY REFERENCE

The present application claims priority under 35 U.S.C. §119 to Japanese Patent Application No. 2006-223986 filed on Aug. 21, 2006. The content of the application is incorporated herein by reference in its entirety.

BACKGROUND OF THE INVENTION

1. Field of the Invention

The present invention relates to an air filtering apparatus that can filter (remove, inactivate, sterilize, etc.) microorganisms (bacteria, virus, fungus, etc. (hereinafter referred to as "virus, etc.") floating in the air.

2. Description of the Related Art

For the purpose of removing microorganisms such as virus, etc. floating in the air, there has been generally proposed an air filtering apparatus in which electrolytic water mist is diffused into the air so as to be brought into direct contact with microorganisms floating in the air, thereby inactivating virus, etc. (for example, JP-A-2002-181358).

The above air filtering apparatus is designed so that the fine particulate electrolytic water mist is diffused to the air, and thus the arrival range of the electrolytic water mist is limited. Accordingly, the electrolytic water mist becomes operative under a use environment the electrolytic water mist is liable to reach, for example, in a relatively small space, however, it hardly become operative under a user environment which the electrolytic water mist hardly reach, for example, in a large space such as a kindergarten, an elementary/junior high/high school, long-term care insurance facilities, a hospital or the like.

SUMMARY OF THE INVENTION

Therefore, the present invention has an object to provide an air filtering apparatus that can also filter air in a large space. Here, the air filtering is broadly defined in this specification, and for example, it means removal, inactivation, sterilization, etc. of microorganisms such as bacteria, virus, fungus, etc. (i.e., virus, etc.) floating in the air.

In order to attain the above object, there is provided an air filtering apparatus comprising: a housing having an air suction port through which air is sucked and an air blow-out port through which air is blown out; an air blower for forming in the housing an air flowing passage through which the air sucked from the air suction port flows to the air blow-out port; an air filtering unit that is disposed on the air flowing passage and brings the air supplied along the air flowing passage into contact with electrolytic water containing active oxygen species to filter the air; an electrolytic water supply unit for electrolyzing prescribed water to generate the electrolytic water and supplying the electrolytic water to the air filtering unit; and a water supply unit having a water stock unit for stocking the prescribed water supplied through a water distributing pipe from an external water supply source, the water stocked in the water stock unit being supplied to the electrolytic water supply unit, wherein the air filtered by the air filtering unit is blown out from the air blow-out port to a room.

According to the above air filtering apparatus, electrolytic water mist is not diffused to the room, but the air supplied through the air flowing passage is brought into contact with the electrolytic water containing active oxygen species in the air filtering unit to filter the air, and then the filtered air is blown out from the air blow-out port by the air blower. Therefore, the indoor can be circulated, and also the filtered air can be also circulated in a large space, that is, the air filtering in the large space can be performed.

Furthermore, the water supply unit for supplying prescribed water to the electrolytic water supply unit does not directly introduce prescribed water supplied from the external water supply source through the water distributing pipe to the electrolytic water supply unit, but the water supply unit supplies water temporarily stocked in the water stock unit to the electrolytic water supply unit. Therefore, most of the construction of the air filtering apparatus can be commonly used for both case where a water supply tank or the like as an internal water supply source for supplying prescribed water to the electrolytic water supply unit is provided in the air filtering apparatus 100 and a case where prescribed water is supplied from the external water supply source through the water distributing pipe 61 as described above. That is, when the water supply tank or the like is provided as the internal water supply source in the air filtering apparatus, the prescribed water is supplied from the water supply port of the water supply tank, whereby the water stocked in the water stock unit 51 can be supplied to the electrolytic water supply unit. Accordingly, most of this construction can be made common with most of the construction that the water supply source for introducing prescribed water to the electrolytic water supply unit is provided at the outside of the air filtering apparatus.

In the above filtering apparatus, the water supply unit may be equipped with a water level detecting unit for detecting the water level of the water stocked in the water stock unit, and a controller for controlling the amount of water stocked in the water stock unit so that the prescribed water is supplied to the water stock unit when the water level detected by the water level detecting unit is lower than a predetermined water level.

In the above air filtering apparatus, it is preferable that the air filtering unit has a gas-liquid contact member having a gas-liquid contact face in which the electrolytic water infiltrates and to which the air is supplied through the air flowing passage, and extra electrolytic water discharged from the gas-liquid contact member is introduced to the water stock unit.

In the above air filtering apparatus, it is preferable that the housing is configured to have a substantially rectangular parallelepiped box shape and used while mounted on a floor, the air suction port is disposed at the lower portion of any one of the front face and side face of the housing, the air blow-out port is disposed at the front side on the top face of the housing, the gas-liquid contact member is erected in the housing so that the gas-liquid contact face thereof is substantially parallel to the front face of the housing, a back side space is defined by the gas-liquid contact face and the back face of the housing, a front side space is defined by the gas-liquid contact face and the front face of the housing, and the air sucked form the air suction port by the air blower is made to flow from the lower portion of the housing upwardly in the back side space, passed through the gas-liquid contact face, and then blown out from the front side space through the air blow-out port.

In the air filtering apparatus, it is preferable that the water supply unit has a connection pipe that has a connection port and connected to the water distributing pipe through the connection port, the connecting pipe being exposed to the outside of the housing.

The above air filtering apparatus preferable further comprises a drain pipe for discharging the water stocked in the water stock unit to the outside of the housing.

In the above air filtering apparatus, it is preferable that the prescribed water is water containing predetermined ion species.

In the air filtering apparatus, it is preferable that the prescribed water is tap water supplied from a water line as the external water supply source.

In the above air filtering apparatus, it is preferable that the active oxygen species contains at least one material selected from the group consisting of hypochlorous acid, ozone and hydrogen peroxide.

According to the present invention, the indoor air is sucked from the air suction port into the housing, the sucked air is brought into contact with the electrolytic water containing the active oxygen species, and then the filtered air is blown out from the air blow-out port.

DETAILED DESCRIPTION OF THE PREFERRED EMBODIMENT

Figure 1:
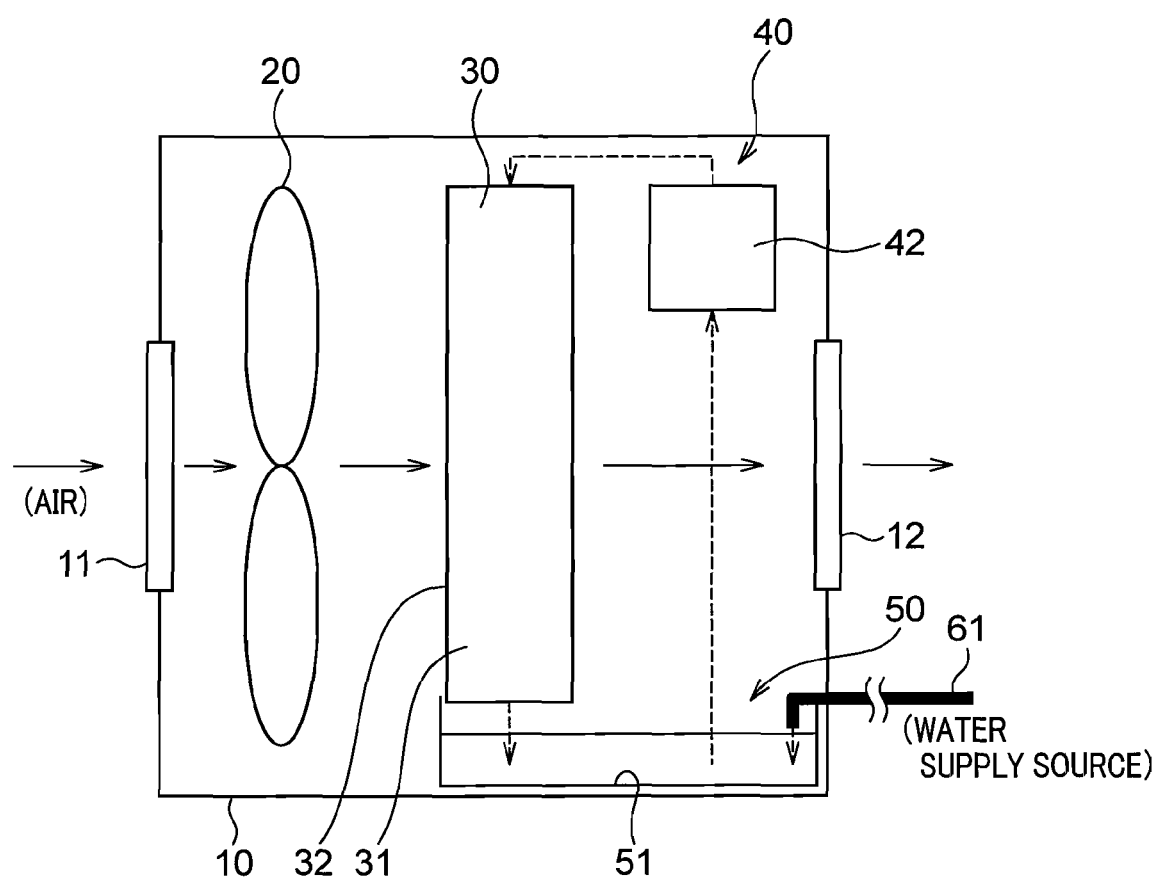
FIG. 1 is a diagram showing the construction of an air filtering apparatus according to an embodiment of the present invention.

A preferred embodiment according to the present invention will be described with reference to the accompanying drawings.

First, the construction of an air filtering apparatus 100 according to an embodiment will be described with reference to FIG. 1.

The air filtering apparatus 100 of this embodiment has a housing 10 having an air suction port 11 and an air blow-out port 12, and also is equipped with an air blower 20, an air filtering unit 30, an electrolytic water supply unit 40 for supplying electrolytic water containing active oxygen species to the air filtering unit 30, and a water stock unit 51 to which water (for example, tap water, city water, well water, etc.) is supplied from an external water supply source through a water distributing pipe 61 and from which the stocked water is supplied to the electrolytic water supply unit 40, these units being disposed in the housing 10.

The air blower 20 forms an air flowing passage along which indoor air sucked through the air suction port 11 from a room where the air filtering apparatus 100 is set up flows to the air blow-out port 12, and it is designed so that a large amount of air flow is supplied to the air filtering unit 30. The air blower 20 is preferably designed so as to supply a proper amount of air flow in accordance with the breadth of the indoor space where the air filtering apparatus 100 concerned is set up. For example, the air flow rate is preferably adjusted in the range from 3 $m^3$/min to 8 $m^3$/min. For example, when air is blown at the air flow rate of 8 $m^3$/min, for an indoor space of about 180 $m^3$ (for example, a classroom of a school or the like), indoor air can be circulated at 2.7 times per hour.

Figure 2:
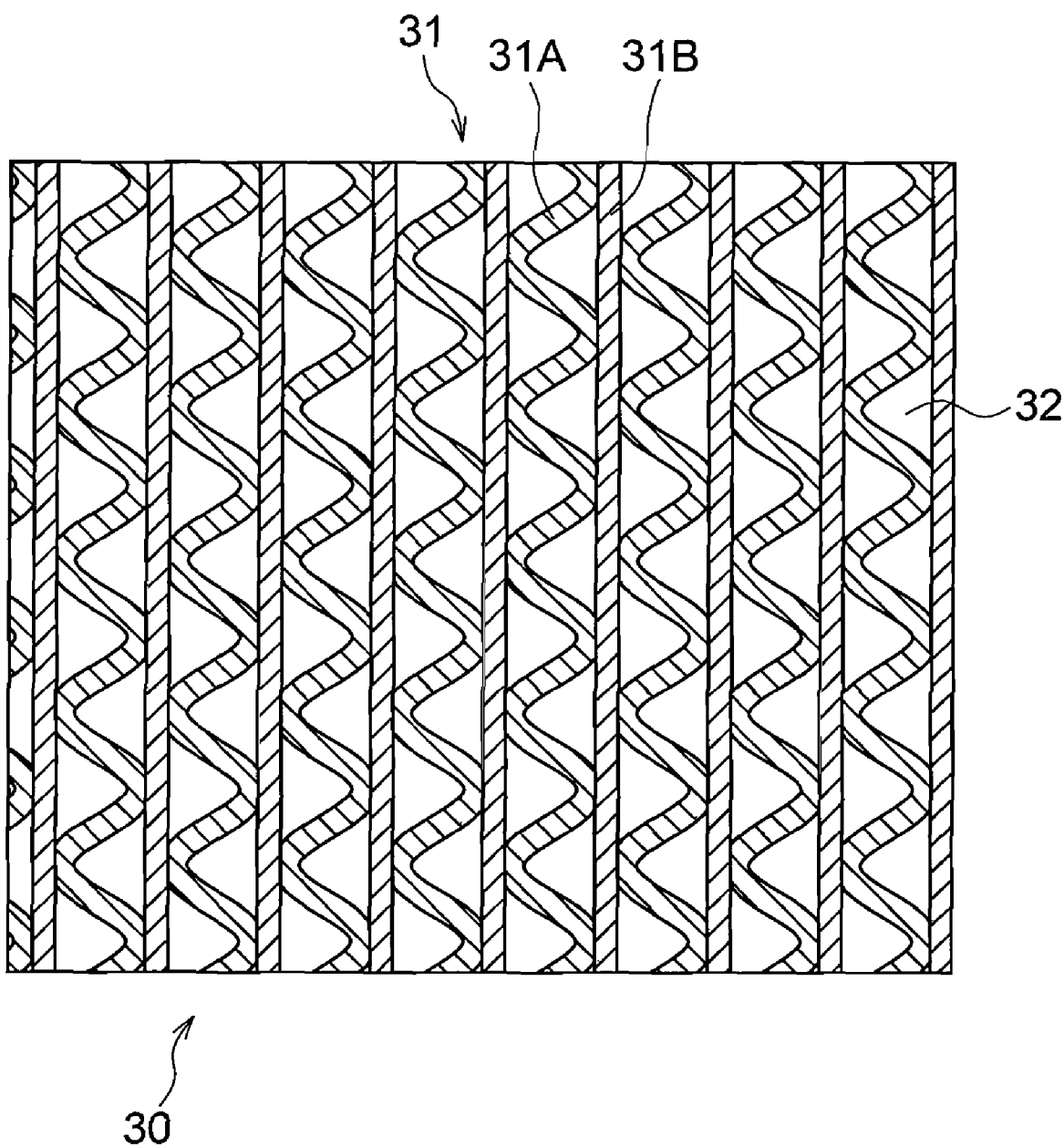
FIG. 2 is a front view showing a gas-liquid contact member applied to an air filtering unit of the embodiment.

A gas-liquid contact member 31 as shown in FIG. 2 may be applied to the air filtering unit 30, for example. The gas-liquid contact member 31 shown in FIG. 2 is a filter member having a honeycomb structure, and it is designed so that the area of a gas contact face 32 is kept large, electrolytic water can be dropped thereto and clogging occurs hardly. That is, the gas-liquid contact member 31 is constructed by joining corrugated members 31A and flat-plate members 31B in a honeycomb shape as a whole.

These members 31A and 31B are formed of raw material having little reactivity to electrolytic water described later, that is, raw material which is little deteriorated by electrolytic water. For example, these members may be formed of polyolefin based resin (polyethylene resin, polypropylene resin or the like), PET (polyethylene terephthalate)resin, vinyl chloride resin, fluorinated resin (PTFE, PFA, ETFE or the like), cellulose based material, ceramics based material or the like.

In this embodiment, these members are formed of PET resin. The gas-liquid contact member 31 may be subjected to a water affinity treatment or the like, so that the gas-liquid contact member 31 has high affinity to electrolytic water. Accordingly, the water retentivity of the gas-liquid contact member 31 to the electrolytic water (wettability) is kept, and the contact between the active oxygen species (described later) and the indoor air can be kept for a long time.

Figure 3A:
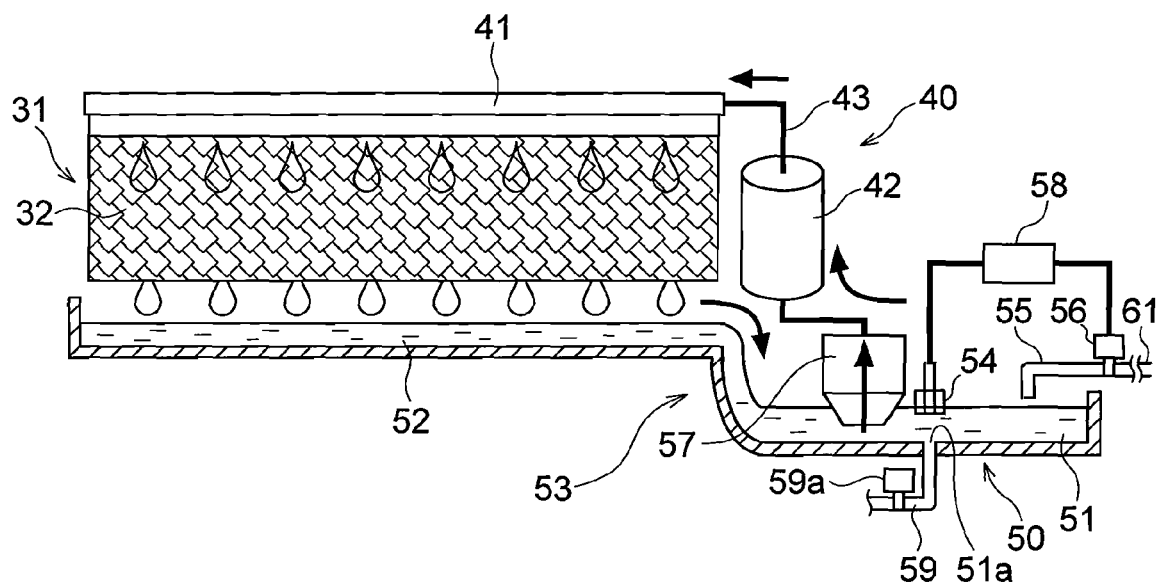
FIG. 3A is a diagram showing the construction of an electrolytic water supply and circulation unit of the embodiment.

As shown in FIG. 3A, a water spray box 41 constituting a part of the electrolytic water supply unit 40 is assembled to the upper portion of the gas-liquid contact member 31, and a water receiving unit 52 constituting a part of the water supply unit 50 is disposed at the lower side of the gas-liquid contact member 31. The water receiving unit 52 receives electrolytic water discharged from the gas-liquid contact member 31 and introduces the electrolytic water to the water stock unit 51. The water receiving unit 52 and the water stock unit 51 are continuously connected to each other and constitute a water receiving tray 53 as a whole.

The electrolytic water supply unit 40 is equipped with an electrolytic bath 42 for generating electrolytic water containing active oxygen species, and an electrolytic water supply pipe 43 for supplying electrolytic water generated in the electrolytic bath 42 to the water spray box 41 in addition to the water spray box 41.

The water spray box 41 is a tubular member assembled to the upper portion of the gas-liquid contact member 31, and plural water spray holes (not shown) are formed at the lower surface of the water spray box 41. Electrolytic water supplied from the electrolytic bath 42 through the electrolytic water supply pipe 43 is dropped and supplied from the water spray holes to the gas-liquid contact member 31, and the gas-liquid contact face 32 is moistened with the electrolytic water while the electrolytic water is infiltrated into the gas-liquid contact member 31.

Figure 3B:
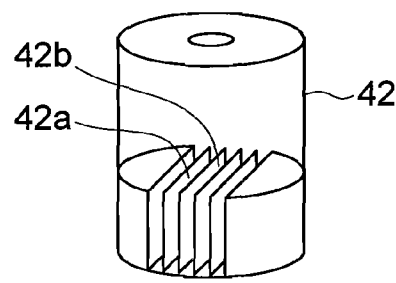
FIG. 3B is a diagram showing the construction of an electrolytic bath.

As shown in FIG. 3B, the electrolytic bath 42 is equipped with at least a pair of electrodes 42a, 42b. When a voltage is applied between the electrodes 42a, 42b, water such as tap water or the like flowing to the electrolytic bath 42 is electrolyzed to generate electrolytic water containing active oxygen species. Here, the active oxygen species means oxygen molecules having higher oxidizing activity than normal oxygen and also related substance thereof, and contain not only so-called narrowly-defined active oxygen such as superoxide anion, singlet oxygen, hydroxyl radical and hydrogen peroxide, but also so-called broadly-defined active oxygen such as ozone, hypochlorous acid, hypohalous acid, etc.

The electrolytic bath 42 is preferably disposed in proximity to the gas-liquid contact member 31. By disposing the electrolytic bath 42 in proximity to the gas-liquid contact member 31, electrolytic water containing active oxygen species achieved by electrolyzing water such as tap water or the like can be immediately supplied to the gas-liquid contact member 31.

The electrodes 42a, 42b may be constructed by two electrode plates each of which comprises a base of Ti (titan) and a coated layer of Ir (iridium), Pt (platinum).

When current is supplied to water by the electrodes 42a, 42b, the following reaction occurs at the cathode:

$$4H^+ + 4e^- + (4OH^-) \rightarrow 2H_2 + (4OH^-)$$

Furthermore, the following reaction occurs at the anode:

$$2H_2O \rightarrow 4H^+ + O_2 + 4e^-$$

At the same time, chlorine ions contained water (chlorine ions are added in tap water in advance) reacts as follows:

$$2Cl^- \rightarrow Cl_2 + 2e^-$$

Furthermore, $Cl_2$ thus generated reacts with water as follows:

$$Cl_2 + H_2O \rightarrow HClO + HCl$$

In this construction, by supplying current to the electrodes 42a, 42b, HClO (hypochlorous acid) having strong sterilizing power, etc. are generated. Therefore, air is passed through the gas-liquid contact member 31 supplied with the filtering water containing this hypochlorous acid to inactivate or sterilize virus, etc. floated in the air passing through the gas-liquid contact member 31, thereby filtering the air, and also breeding of various bacteria, fungus, etc. in the gas-liquid contact member 56 can be prevented. Furthermore, when odor components pass through the gas-liquid contact member 31, the odor components also react with hypochlorous acid in the filtering water, and they are ionized and dissolved in the filtering water, whereby the odor components can be removed from air and thus the air is deodorized.

When electrolytic water is generated, the concentration of the active oxygen species in the electrolytic water is adjusted to such a value that the virus, etc. to be filtered can be inactivated. The adjustment of the concentration of the active oxygen species can be performed by adjusting the voltage applied between the electrodes 42a, 42b and thus adjusting the current value flowing between the electrodes 42a, 42b.

For example, when the current value flowing between the electrodes 42a, 42b is set to 20 mA/cm² in current density, a predetermined free residual chlorine concentration (for example, 1 mg/liter) of hypochlorous acid can be generated. By changing the voltage applied between the electrodes 42a, 42b to adjust the current value, the concentration of the active oxygen species contained in the electrolytic water can be adjusted. Basically, by increasing the current value, the concentration of the active oxygen species in the electrolytic water can be increased.

The water supply unit 50 has the water receiving tray 53 achieved by continuously joining the water stock unit 51 and the water receiving unit 52, a float switch (water level detecting unit) 54 for detecting the water level of water stocked in the water stock unit 51, a connecting pipe 55 connected to an external water distributing pipe 61, a water supply valve 56 provided to the connecting pipe 55, a circulating pump 57 for pumping the water stocked in the water stock unit 51 to the electrolytic bath 42, and a controller 58 (control unit) for controlling the above units.

In the water stock unit 51 are stocked water supplied from the external water supply source through the connecting pipe 55 connected to the water distributing pipe 61, and extra electrolytic water which is discharged from the gas-liquid contact member 31 and received at the water receiving unit 52.

The water supplied from the external water supply source may be tap water, well water, pure water, purified water or the like. In order to conduct electrolysis efficiently in the electrolytic bath 42 or supply ion species required to generate an active oxygen species, water containing a predetermined ion species is preferably used. Therefore, when water containing a small amount of ion species such as well water, pure water, purified water, tap water in some districts or the like is introduced to the electrolytic bath 42, it is preferable that a predetermined ion species required to generate desired active oxygen species is added to the water and stocked in the water stock unit 51. Specifically, when ion-species diluted water is used, it is preferable that a predetermined ion species is added between the external water supply source and the connecting pipe 55 or a predetermined ion species is added to the water stock unit 51.

For example, when hypochlorous acid is generated as active oxygen species, it is assumed that chloride ion exists in water to be introduced into the electrolytic bath 42. Therefore, water containing chloride ion is required to be introduced into the electrolytic bath 42. Here, it is prescribed according to Water Works Law that tap water is disinfected by chlorine or the like to keep sanitary of tap water. Therefore, when tap water is introduced into the electrolytic bath 42, hypochlorous acid can be generated as an active oxygen species with a simple construction by using chloride ion contained in tap water in advance. Furthermore, when ion-species diluted water such as well water or the like is supplied from an external water supply source, the apparatus may be designed so that such water is added with chlorine compound such as salt (NaCl) or the like or another predetermined ion species, electrical conductivity required to conduct electrolysis efficiently is achieved and also an ion species required to generate hypochlorous acid is supplied.

The water receiving unit 52 receives and stocks water (electrolytic water) dropped from the gas-liquid contact member 31. Therefore, it is preferably designed to have such a depth that a predetermined amount of water can be stocked therein, and also water received in the water receiving unit 52 flows into the water stock unit 51.

The water stock unit 51 is formed to have a deeper bottom than the water receiving unit 52, and also the float switch 54 and the suction port 57a of the circulating pump 57 are disposed in the water stock unit 51. The water level in the water stock unit 51 is detected by the float switch 54, and when the water level of the water stocked in the water stock unit 51 is lower than a predetermined water level, the detection signal is input to the controller 58, and the controller 58 opens the water supply valve 56 to supply a required amount of water from the external water supply source through the connecting pipe 55 to the water stock unit 51, whereby the water level in the water stock unit 51 is kept constant.

The water stocked in the water stock unit 51 is pumped up by the circulating pump 57 and supplied to the electrolytic bath 42. That is, the water (electrolytic water) discharged from the gas-liquid contact member 31 is supplied to the electrolytic bath 42 again, whereby the use amount of water to be supplied from the external water supply source to the water stock unit 51 can be reduced.

The water stock unit 51 is provided with a drain hole 51a formed at the bottom portion thereof, and a drain pipe 59 is connected to the drain hole 51a. A drain valve 59a is provided to the drain pipe 59, and the water in the water stock unit 51 can be discharged to the outside through the drain pipe 59 by opening/closing the drain valve 59a.

For example, in the air filtering apparatus 100, when scales are deposited on the electrode (cathode) because of electrolysis of predetermined water in the electrolytic bath 42, the electrical conductivity is lowered, and thus it is difficult to continue the electrolysis. In this case, the polarities of the electrodes 42a, 42b (the plus and minus polarities of the electrodes) are inverted, thereby removing the scales. That is, by conducting the electrolysis while the cathode electrode is set to the anode electrode, the scales deposited on the cathode electrode can be removed. Here, there is provided a scale distribution pipe (not shown) for discharging the scales deposited on the electrodes 42a, 42b from the electrolytic bath 42 to the water stock unit 51 together with the electrolytic water. Accordingly, the scales discharged from the electrolytic bath 42 through the scale distribution pipe to the water stock unit 51, and the scales are further discharged through the drain pipe 59 to the outside.

As described with reference to FIGS. 1 to 3, according to the above construction, the air filtering apparatus is not configured so that electrolytic mist is diffused into a room, but configured so that air supplied through the air flowing passage is brought into contact with electrolytic water containing active oxygen species in the air filtering unit 30 to filter the air, and then the filtered air is blown out from the air blow-out port 12 to the room by the air blower 20. Accordingly, the indoor air can be circulated, and also the filtered air can be circulated in a large space, so that air in a large space can be filtered.

Furthermore, the water supply portion 50 for supplying water to the electrolytic water supply unit 40 does not directly supply water supplied from the external water supply source through the water distributing pipe 61 to the electrolytic water supply unit 40, but it introduces water temporarily stocked in the water stock unit 51 to the electrolytic water supply unit 40. Therefore, most of the construction of the air filtering apparatus can be commonly used for both case where a water supply tank as an internal water supply source for supplying water to the electrolytic water supply unit 40 is provided in the air filtering apparatus 100 and a case where water is supplied from the external water supply source through the water distributing pipe 61 as described above. That is, when the water supply tank or the like is provided as the internal water supply source in the air filtering apparatus 100, the a required amount of prescribed water is supplied from the water supply port of the water supply tank in accordance with the water level of the water stock unit 51, whereby the water stocked in the water stock unit 51 can be supplied to the electrolytic water supply unit 40. Accordingly, most of this construction can be made common with most of the construction that the water supply source for introducing prescribed water to the electrolytic water supply unit 40 is provided at the outside of the air filtering apparatus 100.

Furthermore, when prescribed water is supplied from an external water supply source through the water distributing pipe 61 to the water stock unit 51, the air filtering apparatus 100 can be more miniaturized as compared with the construction that the water supply tank or the like is provided as an internal water supply source in the apparatus.

Next, a specific construction example of the air filtering apparatus 100 of this embodiment will be described with reference to FIGS. 4 to 6.

Figure 4:
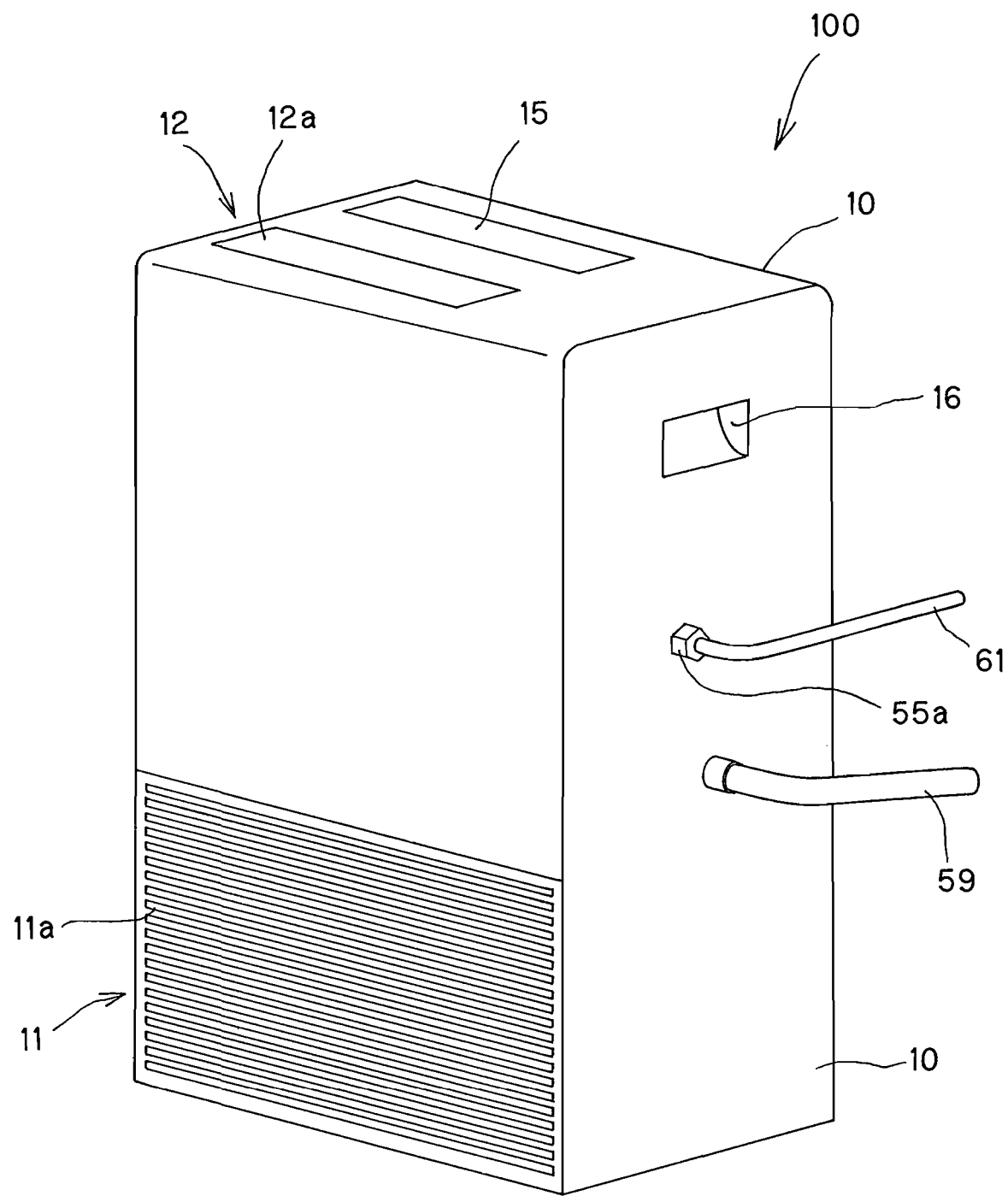
FIG. 4 is a perspective view showing the outlook of the air filtering apparatus of the embodiment.

FIG. 4 is a perspective view showing the outlook of the air filtering apparatus 100 as a specific construction example of the air filtering apparatus 100 (air cleaning apparatus) of this embodiment. The air filtering apparatus 100 shown in FIG. 4 is a floor-mount type air filtering apparatus, and the housing 10 is designed in the form of a vertically-long and substantially rectangular parallelepiped box.

A suction grille 11a is provided at the lower portion of the front face of the housing 10, and it constitutes the air suction port 11. A pre-filter 13 (see FIG. 6) is disposed at the back side of the air suction port 11. The pre-filter 13 collects house dusts such as lint, etc., pollens such as cedar pollen, etc., particulate materials which have relatively large particle sizes and are liable to be precipitated when they float in the air, for example, materials of about 10 μm or more in particle size. By disposing the pre-filter 13 at the back side of the air suction port 11, foreign materials such as lint, pollens, etc. can be prevented from invading into the housing 10.

Furthermore, the air blow-out port 12 is formed on the top face of the housing 10, and a louver 12a is provided as a lid member at the air blow-out port 12. The louver 12a is automatically controlled to change the air blowing direction and also when the air blowing operation of the air filtering apparatus 100 is stopped, the louver 12a is closed to prevent invasion of foreign materials into the housing 10. Furthermore, an air blow-out port filter 14 (see FIG. 6) constructed by a mesh, a woven fabric, a non-woven cloth or the like is disposed at the inside of the louver 12a, whereby foreign materials such as dust, etc. can be prevented from invading into the housing 10 by the air blow-out port filter 14.

Furthermore, an operating panel 15 is provided to the top face of the housing 10. The air blow-out port 12 and the operating panel 15 are formed so as to be elongated along the width direction of the housing 10, and also disposed in parallel to each other. The air blow-out port 12 is disposed at the front side on the top face of the housing 10, and the operating panel 15 is disposed at the back side on the top face of the housing 10.

A recess portion 16 is formed at the upper portion of each of both the side faces of the housing 10. Accordingly, a carrier can lift up and carry the air filtering apparatus 100 by himself/herself while taking hold of the recess portions 16 as grip portions.

A connection port 55a through which the connecting pipe 55 provided in the housing 10 is connected to the water distributing pipe 61 connected to the external water supply source is provided on the right side face of the housing 10 in the front view of the housing 10 so as to be exposed to the outside. Furthermore, the drain pipe 59 is also disposed at the lower side of the connection port 55a on the right side face of the housing 10 so as to extend from the inside of the housing 10 to the outside of the housing 10.

Next, a more detailed construction of each constituent element of the air filtering apparatus 100 and an example of the arrangement in the housing 10 will be described with reference to FIGS. 5 and 6.

Figure 5:
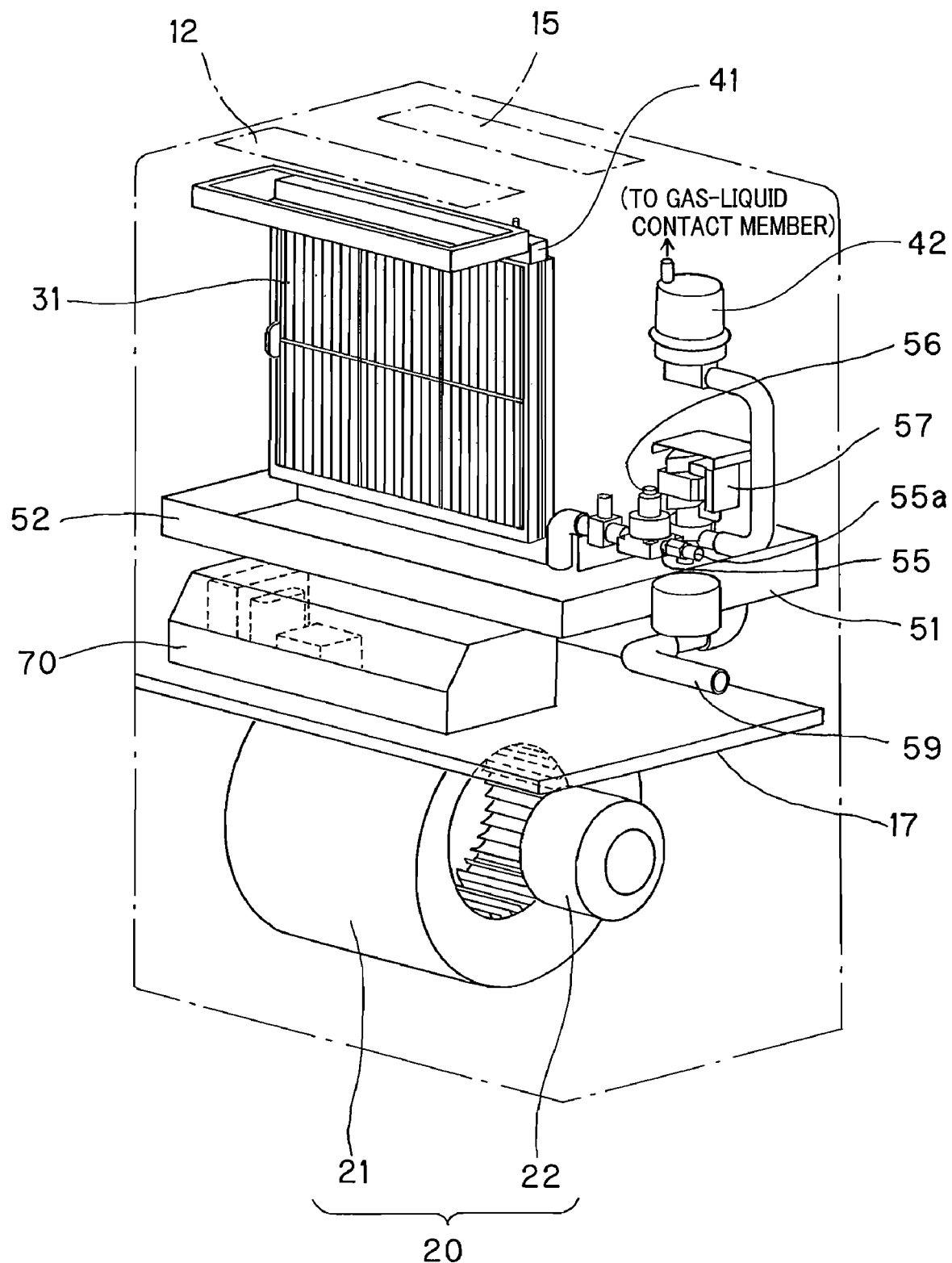
FIG. 5 is a partially broken-out cross-sectional view showing the internal construction of the air filtering apparatus of the embodiment.

FIG. 5 is a perspective view showing the internal construction of the air filtering apparatus 100, and the outlook of the housing 10 is indicated by a virtual line for reference. FIG. 6 is a left-side cross-sectional view.

Figure 6:
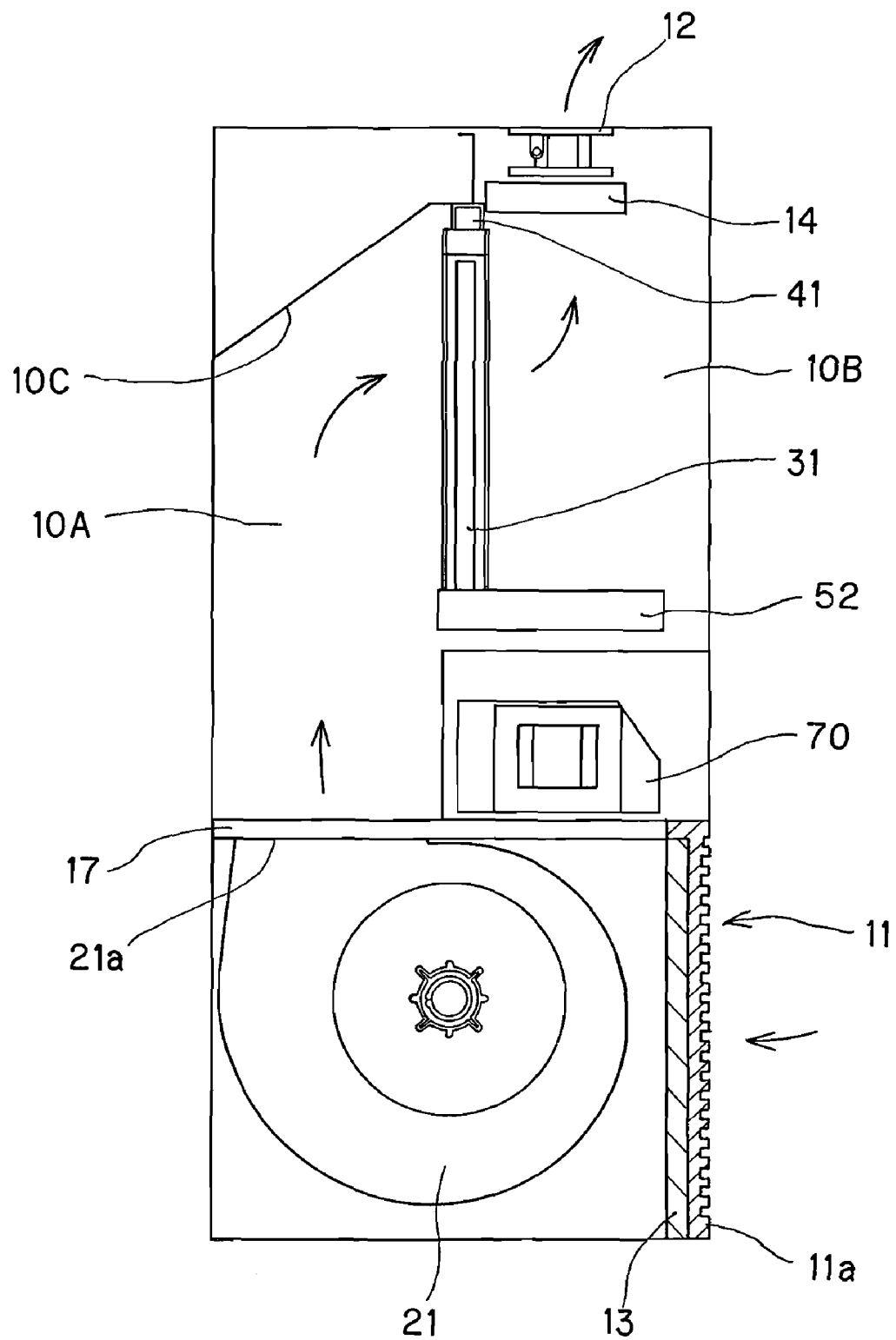
FIG. 6 is a perspective view showing the air filtering apparatus of the embodiment.

As shown in FIGS. 5 and 6, a partition plate 17 through which the inside of the housing 10 is divided to upper and lower chambers is provided in the housing 10. The partition plate 17 is located at the substantially upper end of the suction grille 11a. The air blower 20 is disposed below the partition plate 17. The air blower 20 is equipped with an air blowing fan 21, and a driving motor 22 for driving the air blowing fan 21. In the front view of the housing 10, the air blowing fan 21 and the driving motor 22 are disposed at the left and right sides of the housing 10 below the partition plate 17, respectively.

An air blowing port 21a of the air blowing fan 21 is placed face up at the back side portion of the housing 10. An opening (not shown) is formed in the partition plate 17 so as to be located at the upper side of the air blowing port 21a of the air blowing fan 21. This opening inter communicates with a space extending vertically at the back side of the housing 10 (hereinafter referred to as "back side space 10A"). Accordingly, indoor air sucked from the air suction port 11 by the air blowing fan 21 flows from the front side of the lower portion of the housing 10 to the back side of the housing 10, and further flows upwardly in the back side space 10A.

As shown in FIG. 5, the drain pipe 59 is disposed at the right side of the housing 10 above the partition plate 17, the water stock unit 51 of the water receiving tray 53 is disposed at the upper side of the drain pipe 59, and the circulating pump 57 and the electrolytic bath 42 are disposed at the upper side of the water stock unit 51.

Furthermore, an electrical component box 70 is disposed above the partition plate 17 at the left side of the housing 10. In the electrical component box 70 are disposed various kinds of electrical parts such as a power supply circuit for supplying a power supply voltage, a controller for controlling respective parts of the air filtering apparatus 100, etc.

The gas-liquid contact member 31 is disposed above the electrical component box 70 through the water receiving unit 52 of the water receiving tray 53, and the water spray box 41 is assembled to the upper portion of the gas-liquid contact member 31 as described above.

As shown in FIG. 6, the back surface portion of the electrical component box 70, the back surface portion of the water receiving unit 52 and the gas-liquid contact face 32 of the gas-liquid contact member 31 are arranged on a line, whereby the back side space 10A is defined by the back face of the housing 10, the gas-liquid contact member 31, etc., and a front side space 10B is defined between the front face of the housing 10 and the gas-liquid contact member 31.

An air guide plate 10C which is sloped from the back side of the housing 10 to the front side of the housing 10 is provided at the upper portion of the back side space 10A, and the front end of the air guide plate 10C contacts the water spray box 41. Air blown by the air blowing fan 21 is passed through gas-liquid contact member 31 by the air guide plate 10C to the front side space 10B at the upper portion of the back side space 10A, and then passed through the air blow-out port 12 formed at the top face of the housing and blown out to the room.

That is, the following air flowing passage is formed. That is, the air which is sucked from the air suction port 11 provided at the lower portion of the front face (or side face) of the housing 10 by the air blower 20 in the housing 10 is made to temporarily flow to the back side of the housing 10 at the lower portion of the housing 10 and further flow upwardly in the back side space 10A, and then it is passed through the gas-liquid contact face 32 of the gas-liquid contact member 31 to the front side space 10B by the air guide plate 10C, and then blown out from the front side space 10B through the air blow-out port 12 formed on the top face of the housing 10 to the room.

As described above, the air suction port 11 is provided at the lower portion of the housing 10, the air blow-out port 12 is provided to the upper portion of the housing 10, indoor air is sucked from the lower portion of the housing 10, and the filtered air is blown out from the upper portion of the housing 10. Accordingly, air can be smoothly circulated in the room, and the air in the large space can be efficiently filtered. Furthermore, the inside of the housing 10 is divided to the upper and lower chambers by the partition plate 17. The air blower 20 is disposed at the lower chamber, and the air blowing port 21a of the air blowing fan 21 is disposed so as to face the upper portion of the housing 10. In addition, the back side space 10A and the front side space 10B are defined at the upper portion of the housing 10 by the gas-liquid contact member 31, etc., and the gas-liquid contact face 32 of the gas-liquid contact member 31 is erected so as to be substantially parallel to the front face (or back face) of the housing 10. Accordingly, the air flowing passage along which air is supplied to the gas-liquid contact face 32 can be secured, and the respective constituent elements can be disposed in a compact style in the housing 10, so that the apparatus can be made small in size and thickness.

Next, the operation of this embodiment will be described.

By operating the operating panel 15 shown in FIG. 1, the operation of an on-floor mount type air filtering apparatus 100 is started. When the operation of the air filtering apparatus 100 is started, the water supply valve 56 is opened, and a desired amount of prescribed water is supplied from the water supply source through the water distributing pipe 61 and the connecting pipe 55 to the water stock unit 51. Then, the circulating pump 57 is driven, and water stocked in the water stock unit 51 is pumped up and supplied to the electrolytic bath 42.

In the electrolytic bath 42, a predetermined voltage is applied between the electrodes 42a and 42b, and DC current flows between the electrodes 42a and 42b to electrolyze water, thereby generating electrolytic water containing predetermined active oxygen species such as hypochlorous acid or the like. This electrolytic water is introduced into the electrolytic water supply pipe 43, and dropped through the water spray holes (not shown) of the electrolytic water supply pipe 43. The electrolytic water soaks through the upper edge portion of the gas-liquid contact member 31, and gradually infiltrates downwardly.

The air blowing fan 21 is driven by the driving motor 22, and indoor air sucked from the air suction port 11 by the air blowing fan 21 is passed from the air blowing port 21a of the air blower 20 through the air flowing passage indicated by an arrow of FIG. 6 and then through the gas-liquid contact member 31. This indoor air is brought into contact with active oxygen species contained in electrolytic water infiltrating in the gas-liquid contact member 31, and then blown out from the air blow-out port 12 to the room again. At this time, virus, etc. out of floating micro particles contained in the air are inactivated, and gaseous materials such as odor components, etc. are also dissolved in the electrolytic water or react with hypochlorous acid in the electrolytic water when the air passes through the gas-liquid contact member 31, thereby removing these materials from the air and deodorizing the odor components.

Here, the action mechanism of inactivating virus, etc. by active oxygen species will be described by exemplifying a case where influenza virus is inactivated. The active oxygen species functions to break down and vanish (remove) the surface protein (spike) of the virus concerned which is indispensable for infection. When the surface protein of influenza virus is broken down, the influenza virus is not joined to a receptor which is necessary for infection of the virus concerned, so that infection can be prevented. Therefore, influenza virus floating in the air is brought into contact with the electrolytic water containing the active oxygen species in the gas-liquid contact member 31, so that the influenza virus loses so-called infection power, and thus the infection can be prevented. As a result of a verification test which was made in cooperation with Sanitary Environment Research, it has been found that when air in which influenza virus invades is passed through the gas-liquid contact member 31 of this embodiment, 99% or more of the virus concerned can be removed.

The extra electrolytic water is discharged from the gas-liquid contact member 31, and received by the water receiving unit 52. Then, the water stocked in the water receiving unit 52 flows to the water stock unit 51. The water stocked in the water stocked unit 51 is supplied to the electrolytic bath 42 again by the circulating pump 57. When the amount of water is reduced due to vaporization of water or the like in the water stock unit 51, the controller 58 opens the water supply valve 56 on the basis of the detection signal input from the float switch 54, whereby a proper amount of prescribed water is supplied to the water stock unit 51.

When the operation is stopped or maintenance is carried out, the drain valve 59a is opened, and the electrolytic water and/or insoluble materials such as scales, etc. stocked in the water receiving unit 52 and the water stock unit 51 can be discharged through the drain pipe 59 to the outside.

As described above, according to the above construction, the indoor air sucked from the air suction port 11 provided at the lower portion of the front face of the housing 10 is brought into contact with the electrolytic water dropped to the gas-liquid contact member 31, and then the thus filtered air is blown out from the air blow-out port 12 provided at the upper portion of the housing 10. Therefore, even when the on-floor mount type air filtering apparatus 100 is set up in a so-called large space such as a kindergarten, an elementary/junior high/high school, long-term care insurance facilities, a hospital or the like, indoor air which is brought into contact with electrolytic water and thus filtered air can be blown out to a far place in a large space. Therefore, air filtering in a large space can be efficiently performed, and at the same time deodorization can be performed.

Furthermore, in this embodiment, electrolytic water containing active oxygen species containing hypochlorous acid (HClO), etc. is collected in the water receiving unit 52, and flows to the adjacent water stock unit 51. Therefore, no fungus occurs in the water receiving tray 53, and occurrence of slime can be prevented. Accordingly, the cleaning and maintenance frequency of the water receiving tray 53 can be reduced, and thus the labor of the maintenance, etc. can be reduced.

The present invention is not limited to the air filtering apparatus 100 of the above embodiment, and various modifications may be made without departing from the subject matter of the present invention.

For example, in the above embodiment, hypochlorous acid is generated as the active oxygen species. However, Ozone ($O_3$) or hydrogen peroxide ($H_2O_2$) may be generated as the active oxygen species. In this case, when platinum tantalum electrodes are used as the electrodes 42a, 42b, the active oxygen species can be highly efficiently and stably generated from water in which ion species are rare.

At this time, at the anode, the following reaction occurs:

$$2H_2O \rightarrow 4H^+ + O_2 + 4e^-$$

Simultaneously with the above reaction, the following reactions occur, and ozone ($O_3$) is generated.

$$3H_2O \rightarrow O_3 + 6H^+ + 6e^-$$

$$2H_2O \rightarrow O_3 + 4H^+ + 4e^-$$

Furthermore, at the cathode, the following reactions occur:

$$4H^+ + 4e^- + (4OH^-) \rightarrow 2H_2 + (4OH^-)$$

$$O_2^- + e^- + 2H^+ \rightarrow H_2O_2$$

That is, $O_2^-$ generated through the electrode reaction and $H^+$ in solution are bonded to each other to generate hydrogen peroxide ($H_2O_2$).

In this construction, ozone ($O_3$) and hydrogen peroxide ($H_2O_2$) which have strong sterilizing power are generated by supplying current to the electrodes 42a, 42b, and electrolytic water containing ozone ($O_3$) and hydrogen peroxide ($H_2O_2$) can be created. The concentration of ozone or hydrogen peroxide in the filtering water (electrolytic water) is adjusted to a value suitable for inactivate target virus or the like and air is passed through the gas-liquid contact member 31 supplied with the filtering water having this concentration, whereby target virus, etc. floating in the air can be inactivated. Furthermore, even odor reacts with ozone or hydrogen peroxide in the filtering water when passing through the gas-liquid contact member 31, and ionized and dissolved in the electrolytic water, whereby the odor components are removed from the air and thus the air is deodorized.

What is claimed is:

1. An air filtering apparatus comprising:
   a housing having an air suction port through which air is sucked and an air blow-out port through which air is blown out;
   an air blower for forming in the housing an air flowing passage through which the air sucked from the air suction port flows to the air blow-out port;
   an air filtering unit that is disposed on the air flowing passage and brings the air supplied along the air flowing passage into contact with electrolytic water containing active oxygen species to filter the air;
   an electrolytic water supply unit for electrolyzing prescribed water to generate the electrolytic water and supplying the electrolytic water to the air filtering unit, wherein the electrolytic water supply unit is disposed in a circulating path of the electrolytic water; and
   a water supply unit having a water receiving unit for receiving used electrolytic water discharged from the air filtering unit and a water stock unit which is joined with the water receiving unit, said water stock unit having a deeper bottom than said water receiving unit to stock the prescribed water containing water supplied through a water distributing pipe from an external water supply source and the used electrolytic water discharged from the air filtering unit, and
   a circulating pump for pumping, the prescribed water stocked in the water stock unit being supplied to the electrolytic water supply unit;
   wherein the air filtering unit is configured to blow out the filtered air from the air blow-out port to a room.

2. The air filtering apparatus according to claim 1, wherein the water supply unit is equipped with a water level detecting unit for detecting the water level of the water stocked in the water stock unit, and a controller for controlling the amount of water stocked in the water stock unit so that the prescribed water is supplied to the water stock unit when the water level detected by the water level detecting unit is lower than a predetermined water level.

3. The air filtering apparatus according to claim 1, wherein the air filtering unit has a gas-liquid contact member having a gas-liquid contact face in which the electrolytic water infiltrates and to which the air is supplied through the air flowing passage, and extra electrolytic water discharged from the gas-liquid contact member is introduced to the water stock unit.

4. The air filtering apparatus according to claim 3, wherein the housing is configured to have a substantially rectangular parallelepiped box shape and used while mounted on a floor, the air suction port is disposed at the lower portion of any one of the front face and side face of the housing, the air blow-out port is disposed at the front side on the top face of the housing, the gas-liquid contact member is erected in the housing so that the gas-liquid contact face thereof is substantially parallel to the front face of the housing, a back side space is defined by the gas-liquid contact face and the back face of the housing, a front side space is defined by the gas-liquid contact face and the front face of the housing, and the air sucked from the air
    suction port by the air blower is made to flow from the lower portion of the housing upwardly in the back side space, passed through the gas-liquid contact face, and then blown out from the front side space through the air blow-out port.

5. The air filtering apparatus according to claim 1, wherein the water supply unit has a connecting pipe that has a connection port and connected to the water distributing pipe through the connection port, the connecting pipe being exposed to the outside of the housing.

6. The air filtering apparatus according to claim 1, further comprising a drain pipe for discharging the water stocked in the water stock unit to the outside of the housing.

7. The air filtering apparatus according to claim 1, wherein the prescribed water is water containing predetermined ion species.

8. The air filtering apparatus according to claim 7, wherein the prescribed water is tap water supplied from a water line as the external water supply source.

9. The air filtering apparatus according to claim 1, wherein the active oxygen species contains at least one material selected from the group consisting of hypochlorous acid, ozone and hydrogen peroxide.

10. The air filtering apparatus according to claim 3, further comprising a water receiving unit disposed beneath the gas-liquid contact member, wherein the water stock unit is disposed spaced from the water receiving unit and is connected to the water receiving unit, and the circulating pump is disposed at the upper side of the water stock unit.

* * * * *